United States Patent [19]

Merger et al.

[11] 4,386,219

[45] May 31, 1983

[54] HYDROGENATION CATALYSTS FOR THE PREPARATION OF PROPANEDIOLS AND PROCESSES FOR THE PREPARATION OF PROPANEDIOLS, USING SUCH CATALYSTS

[75] Inventors: Franz Merger, Frankenthal; Ernest Miesen; Franz J. Broecker, both of Ludwigshafen; Wolfgang Schroeder, Bad Durkheim; Karl Baer, Weinheim; Juergen Paetsch, Wachenheim; Leopold Hupfer, Friedelsheim, all of Fed. Rep. of Germany

[73] Assignee: BASF Aktiengesellschaft, Ludwigshafen, Fed. Rep. of Germany

[21] Appl. No.: 345,028

[22] Filed: Feb. 2, 1982

Related U.S. Application Data

[62] Division of Ser. No. 280,776, Jul. 6, 1981.

[30] Foreign Application Priority Data

Jul. 23, 1980 [DE] Fed. Rep. of Germany ....... 3027890

[51] Int. Cl.$^3$ ...................... C07C 31/20; C07C 33/26; C07C 31/13; C07C 41/26
[52] U.S. Cl. .................................... 568/853; 568/630; 568/640; 568/809; 568/814; 568/831; 568/838
[58] Field of Search ............... 568/853, 809, 814, 831, 568/838, 630, 640

[56] References Cited

U.S. PATENT DOCUMENTS

| | | | |
|---|---|---|---|
| 4,181,810 | 1/1980 | Immel et al. | 568/831 |
| 4,250,337 | 2/1981 | Hausen et al. | 568/853 |
| 4,273,939 | 6/1981 | Barnett et al. | 568/814 |
| 4,308,176 | 12/1981 | Kristiansen | 252/463 |

*Primary Examiner*—Joseph E. Evans
*Attorney, Agent, or Firm*—John H. Shurtleff

[57] ABSTRACT

Hydrogenation catalysts, which have a specific surface area of from 50 to 150 square meters per gram, solely or partially contain crystals having a spinel structure and copper in the form of copper oxide, and have been obtained by precipitating copper and aluminum in a ratio of from 0.25 to 3 atoms of copper per atom of aluminum from their compounds in the presence of a carbonate at a pH of from 4.5 to 9 and calcining the resulting precipitate at from 300° to 800° C., for the catalytic preparation of propanediols by hydrogenating hydroxypropionaldehydes at not more than 300 bar pressure and from 50° to 200° C., and processes for the preparation of propanediols by the use of such catalysts.

The propanediols obtainable by the process of the invention, in particular 2,2-dimethylpropane-1,3-diol, are valuable starting materials for the preparation of lubricants, plastics, surface coatings and synthetic resins, for example corresponding polyesters.

14 Claims, No Drawings

HYDROGENATION CATALYSTS FOR THE PREPARATION OF PROPANEDIOLS AND PROCESSES FOR THE PREPARATION OF PROPANEDIOLS, USING SUCH CATALYSTS

This is a division of application Ser. No. 280,776, filed July 6, 1981.

The present invention relates to hydrogenation catalysts, which have a specific surface area of from 50 to 150 square meters per gram, solely or partially contain crystals having a spinel structure and copper in the form of copper oxide, and have been obtained by precipitating copper and aluminum in a ratio of from 0.25 to 3 atoms of copper per atom of aluminum from their compounds in the presence of a carbonate at a pH of from 4.5 to 9 and calcining the resulting precipitate at from 300° to 800° C., for the catalytic preparation of propanediols by hydrogenating hydroxypropionaldehydes at not more than 300 bar pressure and from 50° to 200° C., and processes for the preparation of propanediols by the use of such catalysts.

The hydrogenation of hydroxypivalaldehyde and other hydroxypropionaldehydes is conventionally carried out in the liquid phase at pressures of from 100 to 200 bar and at up to 150° C., using nickel, nickel-copper and cobalt catalysts (German Published Application DAS No. 1,014,089). German Laid-Open Application DOS 1,804,984 No. describes the hydrogenation at 175°–220° C. and 64–704 bar in the presence of a copper chromite catalyst. This patent points out (page 10, last paragraph) that the choice of the catalyst employed is a critical factor, since the hydrogenation takes place in the presence of formaldehyde and water. Most conventional hydrogenation catalysts are deactivated by formaldehyde. Furthermore, water has an adverse effect on the activity and stability of most carrier materials. With nickel and cobalt catalysts, undesired by-products are formed under the conditions mentioned, and these adversely affect the yield and purity of the neopentyl glycol. The process requires special operations in order to make the hydroxypropionaldehyde capable of hydrogenation. In a first treatment stage, lower-boiling constituents, alcohols and excess isobutyraldehyde are distilled off; in the second treatment stage, the hydroxypivalaldehyde is extracted from the aqueous saline solution by means of an organic, water-insoluble solvent, and the resulting organic solution of hydroxypivalaldehyde is washed salt-free with pure water. In the third treatment stage, the solution is dried. These measures are necessary to protect the catalyst in the hydrogenation reactor from deactivating factors, especially from an excessively high concentration of water during hydrogenation.

The catalyst used in the above process furthermore has the disadvantage of a relatively low activity. Thus, even the hydrogenation of hydroxypivalaldehyde alone requires, in every Example, a temperature of 210° C. and a hydrogen pressure of 353 bar. Whilst the solution containing hydroxypivalaldehyde is being heated to this temperature, a Tishtchenko reaction results in the formation of esters which can only be hydrogenated at 200°–210° C. and hydrogen pressures of 353–423 bar.

In another process (British Pat. No. 1,048,530) 2,2-dimethyl-3-hydroxypropanol is hydrogenated simultaneously with isobutyraldehyde over a copper/chromium oxide catalyst. In this process, again, numerous by-products are formed to a significant degree. A commercial limitation of the process is the need for further conversion of the isobutanol produced. To achieve satisfactory yields, extreme hydrogenation conditions must be employed, with expensive recycling. The working up, or disposal (entailing considerable loss of material), of the aqueous phase can also be very expensive.

The process requires hydrogenation temperatures of from 175° to 220° C., especially from 190° to 220° C., and hydrogen pressures of from 63 to 420 bar, especially from 147 to 322 bar. These high temperatures and pressures are evidently again required because of the esters formed during the reaction.

In a further process (German Published Application DAS No. 2,054,601) the reaction mixture coming from a synthesis state and containing hydroxypivalaldehyde and lower-boiling solvents is vaporized and passed, together with the hydrogen to be used for the hydrogenation, over a hydrogenation catalyst which preferably consists of nickel. Disadvantages of the vaporization are the energy required and the formation of by-products in this process step.

German Published Application DAS No. 1,957,551 discloses that neopentyl glycol can be prepared by reacting isobutyraldehyde with formaldehyde in the presence of a basic catalyst and then hydrogenating the resulting 2,2-dimethyl-3-hydroxypropanal in the presence of a hydrogenation catalyst. Hydrogenation catalysts mentioned are cobalt, copper, manganese and/or nickel catalysts, for example in the form of sintered catalysts. Preferably, phosphoric acid is used as an additional component. In the Examples, high hydrogenation temperatures are employed, and only through these are satisfactory space-time yields achieved. The pressures to be employed are in the range from 150 to 300 bar. Accordingly, this process entails the use of expensive high pressure apparatus, and considerable energy expenditure for compression.

We have found that propanediols of the formula

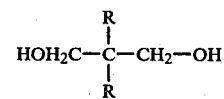
                                              I where the individual radicals R can be identical or different and each is an aliphatic, araliphatic or aromatic radical, or the two radicals R together with the adjacent carbon atom are members of an alicyclic ring, are obtained in an advantageous manner by hydrogenating an aldehyde in the presence of a copper-containing hydrogenation catalyst, if the hydrogenation is carried out with a hydroxypropionaldehyde of the formula

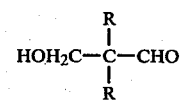
                                              II where R has the above meanings, under a pressure of at most 300 bar, at a hydrogenation temperature of from 50° to 200° C., and with a hydrogenation catalyst which has a specific surface area of from 50 to 150 square meters per gram, solely or partially contains crystals having a spinel structure and copper in the form of copper oxide, and has been obtained by precipitating copper and aluminum in a ratio of from 0.25 to 3 atoms of copper per atom of aluminum from their compounds in the presence of a carbonate at a pH of from 4.5 to 9 and calcining the resulting precipitate at from 300° to 800° C.

Further, we have found the novel hydrogenation catalysts for the preparation of propanediols of the formula

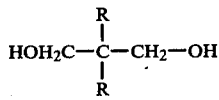

where the individual radicals R can be identical or different and each is an aliphatic, araliphatic or aromatic radical, or the two radicals R together with the adjacent carbon atom are members of an alicyclic ring, by hydrogenating a hydroxypropionaldehyde of the formula

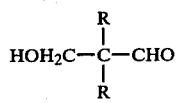

where R has the above meanings, in the presence of a copper-containing hydrogenation catalyst, said catalysts being used under a pressure of at most 300 bar and at a hydrogenation temperature of from 50° to 200° C., having a specific surface area of from 50 to 150 square meters per gram, solely or partially containing crystals having a spinel structure and copper in the form of copper oxide, and having been obtained by precipitating copper and aluminum in a ratio of from 0.25 to 3 atoms of copper per atom of aluminum from their compounds in the presence of a carbonate at a pH of from 4.5 to 9 and calcining the resulting precipitate at from 300° to 800° C.

Where hydroxypivalaldehyde is used, the reaction can be represented by the following equation:

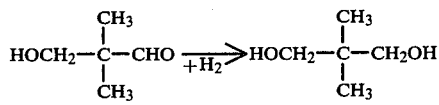

Compared to the conventional processes, the process according to the invention gives propanediols, especially neopentyl glycol, more simply and more economically, in good yield and high purity, without substantial formation of by-products, for example esters and acetals, or of decomposition products. Additional purification operations to remove impurities in the starting material before carrying out the hydrogenation are not necessary. The high hydrogenating activity of the catalysts according to the invention allows the hydrogenation to be carried out at low pressures and low temperatures, so that there is no hydrogenolytic cleavage of, for example, the neopentyl glycol formed. The reverse decomposition of hydroxypivalaldehyde to isobutyraldehyde and formaldehyde is also not observed. Even crude reaction mixtures from the preparation of the aldehyde can be fed directly to the hydrogenation reactor. The catalysts have a longer life; after 10,000 operating hours, their activity remains virtually at the initial level, and their mechanical properties are satisfactory. Expensive high pressure apparatus is not needed. Ester formation by a Tishtchenko reaction is avoided. All these advantageous results are surprising in view of the prior art. Thus, the high space-time yields of the process according to the invention would not have been expected in view of the low temperatures and pressures and the danger of this being associated with lesser hydrogenation and the decomposition of by-products, resulting in increased formation of heterogeneous mixtures.

An essential feature of the process according to the invention is that the hydrogenation catalyst is prepared entirely or partially from mixed crystals which have a specific structure; this structure, during the subsequent thermal decomposition (calcination), maintains the fine distribution and special configuration of copper and aluminum in the finished, ie., calcined, catalyst. It is this configuration which is responsible for the advantageous results obtained according to the invention. The copper/aluminum/OH/CO$_3$ mixed crystals formed completely or partially as a result of the precipitation reaction have a defined and measurable crystal lattice. Preferably, the crystals have a layer structure. The individual lattice sites are occupied by copper and aluminum as well as by the radicals CO$_3$ and OH, and by H$_2$O; furthermore additives, as a rule in an amount of from 0 to 10, especially from 0 to 5, percent by weight, based on total catalyst, can occupy lattice sites. Suitable additives are chromium, calcium, cobalt or magnesium, which, in the form of their carbonates, hydroxides or oxides, occupy lattice sites or defects; if desired, the additives may also be used, in an amorphous or crystalline form, as a physical mixture with the mixed crystals according to the invention.

In the finished, calcined catalyst, advantageously from 3 to 90 percent by weight, especially from 20 to 80 percent by weight, consist of crystals of the spinel type. For details concerning the structure of the spinel type, reference may be made to Ullmanns Encylklopädie der technischen Chemie, volume 6, pages 242–244. The structure can correspond to natural or synthetic pure spinel, as well as to reddish, blue, black, greenish blue, yellowish green, green, emerald, pinkish red or bluish red spinels, spinel-like sapphire or alexandrite-like spinel.

The catalyst contains from 0.25 to 3, especially from 0.5 to 3, atoms of copper per atom of aluminum. Advantageously, the catalyst has a specific surface area of from 50 to 120 square meters, preferably from 60 to 120 square meters, especially from 60 to 100 square meters, per gram. Furthermore, it contains all or part, advantageously from 3 to 50 percent by weight, especially from 3 to 30 percent by weight, of the total copper in the form of copper-II oxide. Advantageously, the catalyst has certain other specific structural characteristics, namely a mean pore radius of from 2,000 to 8,000, preferably from 4,000 to 7,000, nanometers and a pore volume of from 0.3 to 6, preferably from 0.4 to 1, cubic centimeter per gram.

Preferred starting materials II and accordingly preferred end products I are those where the individual radicals R are identical or different and each is alkyl of 1 to 6 carbon atoms, aralkyl or alkylaryl of 7 to 12 carbon atoms, or phenyl, or the two radicals R together with the adjacent carbon atom are members of a 5-membered or 6-membered alicyclic ring. The above radicals and rings can additionally be substituted by groups which are inert under the reaction conditions, for example alkyl or alkoxy, each of 1 to 4 carbon atoms.

Examples of suitable starting materials II are 3-hydroxypropionaldehydes which in the 2-position have two identical or different substituents chosen from amongst methyl, ethyl, propyl, isopropyl, butyl, isobutyl, sec.-butyl, tert.-butyl, benzyl, phenyl, 2-methylphenyl, 3-methylphenyl, 4-methylphenyl, 3-methoxyphenyl, 2-methoxyphenyl and 4-methoxyphenyl. Further examples are 1-formyl-1-methylolcyclohexane and 1-formyl-1-methylolcyclopentane.

The precipitation is advantageously carried out from an aqueous solution of copper salts and aluminum salts, with or without additives, by means of a carbonate or, where appropriate, a hydroxide. Examples of suitable salts are the acetates, chlorides, sulfates, bicarbonates, bisulfates and especially nitrates of copper, aluminum and the additive metals. The carbonate radicals in the catalyst can be introduced into the precipitation bath in the form of corresponding carbonates of copper, aluminum or additive metal or advantageously in the form of additional alkali metal carbonates or alkali metal bicarbonates which serve to give the pH value required according to the invention, for example the potassium salts or sodium salts. The catalyst employed according to the invention is advantageously prepared by using two aqueous solutions, with solution 1 containing the nitrates of copper, aluminum and additive metal, if any, whilst solution 2 consists of an aqueous sodium carbonate or bicarbonate solution.

Advantageously, a 1–3-molar solution of the metal compounds and a 1–3-molar carbonate solution or bicarbonate solution is employed. When a mixture of carbonates and hydroxides, as a rule alkali metal hydroxides, is used, the proportion of carbonate is advantageously from 25 to 95 percent by weight of the mixture. The precipitation is advantageously carried out at from 5° to 90° C., preferably from 20° to 90° C., advantageously from 40° to 85° C., more especially from 60° to 80° C., for from 1 to 2 hours, batchwise or continuously, under superatmospheric pressure or, advantageously, at atmospheric pressure. Preferably, both solutions are introduced into a stirred kettle heated to the precipitation temperature. The pH mentioned below is maintained, during this parallel precipitation by regulating the feed rates. The precipitation can be carried out in a single stage, in general at a pH of from 6.9 to 9, especially from 7 to 8.5. Advantageously, however, it is carried out in two pH stages, the first at a pH of from 4.5 to 6.5, preferably from 5 to 6, and the second at a pH of from 6.8 to 9, preferably from 7 to 8. The precipitate formed is then advantageously filtered off and washed salt-free, for example nitrate-free, with water. Another possible way of removing salt from the precipitate is to wash the latter with very dilute sodium hydroxide solution, for example a solution diluted to pH 10, advantageously until the pH in the wash water reaches from 7.8 to 9.5 after filtration. When nitrates are used, the nitrate can also be removed from the precipitate with 0.1–1, preferably 0.2–0.3, percent strength by weight aqueous $CO_2$ solution; this dissolves from 5 to 20 percent by weight of the precipitated copper. The washed precipitate is then dried, advantageously at 100°–120° C., and is then advantageously molded and thereafter calcined at from 300° to 800° C., preferably from 500° to 700° C., advantageously for from 0.2 to 2 hours. During molding, the dried catalyst is brought to the desired shape, for example tablets or extrudates. It is also possible to calcine the dried catalyst at the above temperature, for example for from 0.1 to 2 hours, and then to mold it, for example to tablets or extrudates; after the catalyst has been molded, it is advantageous to heat it once again, for example for from 0.1 to 2 hours at from 200° to 350° C. To develop their particular properties and display their full activity, the catalysts as a rule require this special heating after filtration and drying. In the course of this heating, recrystallization occurs and copper oxide and crystals having a spinel structure are formed, as can be confirmed by X-ray structural analysis. On calcination, the catalyst in general shrinks to 55–75 percent of its volume before being heated again. The specific surface area developed conforms with that required according to the invention. If the catalyst contains $Na_2O$ or other alkali metal oxides in amounts greater than 0.3 percent by weight, based on the catalyst, higher temperatures (calcination), for example from 610° to 750° C., are advantageous. In producing extrudates, it is advantageous to employ powder which has already been calcined. For catalysts of relatively low aluminum content, calcining temperatures of from 300° to 600° C. are advantageous. The loss of weight of the finished catalyst on heating at 900° C. is less than 1.5 percent by weight.

In a preferred embodiment, the catalyst, prepared as above, is activated at 150°–250° C. with a mixture of from 0.5 to 30 parts by volume of hydrogen and 99.5 to 70 parts by volume of nitrogen, using from 50 to 1,000 liters of this mixture per liter of catalyst per hour. After activation the catalyst is advantageously wetted with water or with the hydrogenation mixture containing neopentyl glycol.

The hydrogenation of the hydroxypropionaldehyde II, especially of the hydroxypivalaldehyde, is advantageously carried out batchwise or, preferably, continuously, at from 50° to 200° C., preferably from 70° to 175° C., especially from 80° to 150° C., under a pressure of from 1 to 300 bar, preferably from 10 to 200 bar, especially from 20 to 100 bar.

In batchwise hydrogenations, the catalyst is advantageously used in an amount of from 1 to 10, especially from 2 to 5, percent by weight, based on hydroxypropionaldehyde II, especially hydroxypivalaldehyde, with a reaction time of from 0.1 to 5 hours. The continuous hydrogenation is advantageously carried out by conventional techniques, for example by an ascending-flow process or trickle process in a fixed bed reactor, at the temperatures and pressures stated above. A hydroxypivalaldehyde solution, advantageously an aqueous solution, where appropriate containing recycled material, is introduced continuously into the reactor, advantageously by means of injection pumps, under the preferred conditions, in an amount of from 0.1 to 35 parts of hydroxypropionaldehyde per part by volume of catalyst per hour. The material leaving the reactor is either fed directly into a continuously operating fractionation column or is collected in stock vessels and fractionated batchwise. In general, the distillation pressure is chosen so that the boiling point of the end product is higher than its melting point (129° C.), ie. above 50 mbar.

In a preferred embodiment, the reaction mixture from the preparation of the starting material II is used instead of the material II itself; for example, instead of an aqueous hydroxypivalaldehyde solution, the mixture from the reaction of isobutyraldehyde with formaldehyde is used (this reaction preferably being carried out with from 0.1 to 1.5, advantageously from 0.9 to 1.1, moles of formaldehyde per mole of isobutyraldehyde, in the presence of a tertiary amine catalyst, advantageously at from 20° to 100° C., under atmospheric or superatmospheric pressure, batchwise—for example for from 0.1 to 4 hours—or continuously).

The propanediols obtainable by the process of the invention, in particular 2,2-dimethylpropane-1,3-diol, are valuable starting materials for the preparation of lubricants, plastics, surface coatings and synthetic resins, for example corresponding polyesters. Concerning use, reference may be made to the publications mentioned and to Ullmans Encyklopädie der technischen Chemie, volume 15, pages 292 et seq.

In the Examples, parts are by weight and bear the same relation to parts by volume as that of the kilogram to the liter.

EXAMPLE 1

(a) Preparation of the catalyst: 1,200 parts by volume of 27 percent strength by weight NaNO₃ solution are introduced into a 1st stirred kettle and heated to 80° C.; 1,200 parts by volume per hour of an aqueous solution containing 2.72 percent by weight of Al and 4.8 percent by weight of Cu, in the form of their nitrates, are added at the same temperature, whilst stirring. Simultaneously, a 20 percent strength by weight aqueous sodium carbonate solution is added in portions so as to set up and maintain a pH of 5.5 in the kettle. The precipitation mixture is transferred to a second stirred kettle at 70° C., and after 8,000 parts by volume have been introduced, the pH is raised to 7 with 20 percent strength by weight sodium carbonate solution. The precipitate is stirred for one hour whilst constantly introducing air or an inert gas; in the course thereof the pH rises to 7.9. The mixture is then filtered and the product washed nitrate-free with water. The paste left on the filter is dried in a spray tower using hot air at 120° C. exit temperature, and the product is tableted, using one percent by weight of graphite as an auxiliary.

The tablets obtained are then calcined for 60 minutes in a heated rotary furnace at 620° C. In the furnace, the tablet diameter shrinks from its original value of 4.75 millimeters to 4.15 millimeters. The catalyst contains 0.75 atom of Cu per atom of Al. The specific surface area is 80 m²/g. The X-ray structural analysis indicates a lattice of CuO and of a well-developed spinel. The weight loss on heating is 0.3 percent at 900° C.

(b) Hydrogenation: 1 part of the catalyst prepared as described in (a), in the form of pills, is introduced into a hydrogenation reactor and reduced under atmospheric pressure, at from 100° to 200° C., with 200 parts by volume of a mixture of 5 percent by volume of H₂ and 95 percent by volume of N₂, using 300 parts by volume of mixture per part by volume of catalyst per hour. After having been activated, the catalyst is cooled to 110° C. and thereafter 0.4 part per hour of a 60 percent strength by weight aqueous solution of hydroxypivalaldehyde (the hydroxypivalaldehyde being 98% pure, the impurities being isobutyraldehyde and formaldehyde) is passed from a stock vessel through the reactor and is hydrogenated at 100° C. and 30 bar with pure hydrogen, 2 parts of reaction product being recycled at the same time, to provide better heat removal and wetting of the catalyst. The throughput is 0.24 part of hydroxypivalaldehyde per part of catalyst per hour. The conversion is 98 percent. The hydrogenated mixture is freed from the catalyst by filtration and is then fractionated by distillation through a packed glass column. 100 parts of hydrogenated mixture, distilled under 90 mbar, give first runnings of water and small amounts of methanol, isobutanol and hydroxypivalaldehyde, followed by 54 parts of neopentyl glycol of boiling point 138°–140° C., corresponding to 93% of theory, based on starting material. The ester content is less than 0.1 percent by weight.

EXAMPLE 2

(a) Preparation of the catalyst: An aqueous nitrate solution which contains 9.8% of Cu and 1.39% of Al is reacted, by a method similar to Example 1a, with a 20 percent strength sodium carbonate solution at 80° C. and pH 5.5, in a stirred kettle with an overflow. The throughput is 1,000 parts of nitrate solution per hour. The reaction in the second stirred kettle, and the working up and tableting, are carried out similarly to Example (1a). The calcination is carried out for one hour at 400° C. The catalyst contains crystals with a spinel structure and copper in the form of copper oxide; the specific surface area is 80 square meters per gram.

(b) Hydrogenation: One part of the catalyst prepared as described in (a), in the form of pills, is introduced into a hydrogenation reactor and reduced under atmospheric pressure, at 200° C., with 200 parts by volume of a mixture of 5 percent by volume of H₂ and 95 percent by volume of N₂, using 300 parts by volume of mixture per part by volume of catalyst per hour. After having been activated, the catalyst is cooled to 100° C. and thereafter 0.3 part per hour of a 60 percent strength by weight aqueous solution of hydroxypivalaldehyde (the hydroxypivalaldehyde being 98% pure, the impurities being isobutyraldehyde and formaldehyde) is passed from a stock vessel through the reactor and is hydrogenated at 100° C. and 30 bar. The throughput is 0.13 part of hydroxypivalaldehyde per part by volume of catalyst per hour. The conversion is 98 percent. The hydrogenated mixture is freed from the catalyst by filtration, and is then fractionated by distillation through a packed glass column. 100 parts of hydrogenated mixture, distilled under 90 mbar, give first runnings of water and small amounts of methanol, isobutanol and hydroxypivalaldehyde, followed by 54.7 parts of neopentyl glycol of boiling point 138°–140° C., corresponding to 93% of theory, based on starting material. The ester content is less than 0.1 percent by weight.

We claim:

1. A process for the preparation of propanediols of the formula

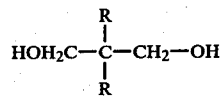

$$HOH_2C-\underset{\underset{R}{|}}{\overset{\overset{R}{|}}{C}}-CH_2-OH \qquad I$$

where the individual radicals R can be identical or different and each is an aliphatic, araliphatic or aromatic radical, or the two radicals R together with the adjacent carbon atom are members of an alicyclic ring, by hydrogenating an aldehyde in the presence of a copper-containing hydrogenation catalyst, wherein the hydrogenation is carried out with a hydroxypropionaldehyde of the formula

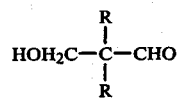

$$HOH_2C-\underset{\underset{R}{|}}{\overset{\overset{R}{|}}{C}}-CHO \qquad II$$

where R has the above meanings, under a pressure of at most 300 bar, at a hydrogenation temperature of from 50° to 200° C., and with a hydrogenation catalyst which has a specific surface area of from 50 to 120 square meters per gram, solely or partially contains crystals having a spinel structure and copper in the form of copper oxide, and has been obtained by precipitating copper and aluminum in a ratio of from 0.25 to 3 atoms of copper per atom of aluminum from their compounds in the presence of a carbonate at a pH of from 4.5 to 9 and calcining the resulting precipitate at from 300° to 800° C.

2. A process as claimed in claim 1, wherein the reaction is carried out with additives in an amount of from 0 to 10 percent by weight, based on total catalyst.

3. A process as claimed in claim 1, wherein the catalyst contains from 3 to 90 percent by weight of crystals of the spinel type.

4. A process as claimed in claim 1, wherein the catalyst contains from 0.5 to 3 atoms of copper per atom of aluminum.

5. A process as claimed in claim 1, wherein the catalyst has a specific surface area of from 60 to 120 square meters per gram.

6. A process as claimed in claim 1, wherein from 3 to 50 percent by weight of the total copper in the catalyst is in the form of copper-II oxide.

7. A process as claimed in claim 1, wherein the catalyst has a mean pore radius of from 2,000 to 8,000 nanometers and a pore volume of from 0.3 to 6 cubic centimeters per gram.

8. A process as claimed in claim 1, wherein the precipitation is carried out at from 5° to 90° C.

9. A process as claimed in claim 1, wherein the precipitation is carried out with 1–3-molar solutions of the metal compounds and 1–3-molar carbonate solutions or bicarbonate solutions.

10. A process as claimed in claim 1, wherein the precipitation is carried out at a pH of from 6.9 to 9.

11. A process as claimed in claim 1, wherein the catalyst has been activated at from 150° to 250° C. with a mixture of from 0.5 to 30 parts by volume of hydrogen and from 99.5 to 70 parts by volume of nitrogen, used at the rate of from 50 to 1,000 liters of mixture per liter of catalyst per hour.

12. A process as claimed in claim 1, wherein the reaction is carried out at from 70° to 175° C.

13. A process as claimed in claim 1, wherein the reaction is carried out under a pressure of from 1 to 300 bar.

14. A process as claimed in claim 1, wherein the reaction is carried out using from 0.1 to 35 parts of hydroxypropionaldehyde per part by volume of catalyst per hour.

* * * * *